(12) United States Patent
Matsumoto

(10) Patent No.: US 10,646,114 B2
(45) Date of Patent: May 12, 2020

(54) OPHTHALMIC IMAGING APPARATUS AND METHOD OF CONTROLLING THE SAME

(71) Applicant: CANON KABUSHIKI KAISHA, Tokyo (JP)

(72) Inventor: Kazuhiro Matsumoto, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 108 days.

(21) Appl. No.: 15/942,666

(22) Filed: Apr. 2, 2018

(65) Prior Publication Data
US 2018/0289251 A1  Oct. 11, 2018

(30) Foreign Application Priority Data
Apr. 6, 2017  (JP) .................. 2017-075964

(51) Int. Cl.
*A61B 3/00* (2006.01)
*A61B 3/14* (2006.01)
*A61B 3/10* (2006.01)

(52) U.S. Cl.
CPC ............ *A61B 3/0008* (2013.01); *A61B 3/102* (2013.01); *A61B 3/14* (2013.01)

(58) Field of Classification Search
CPC ................................ A61B 3/0008; A61B 3/14
See application file for complete search history.

(56) References Cited

U.S. PATENT DOCUMENTS

| | | |
|---|---|---|
| 4,820,037 A | 4/1989 | Kohayakawa et al. |
| 4,848,896 A | 7/1989 | Matsumoto |
| 4,952,049 A | 8/1990 | Matsumoto |
| 5,076,274 A | 12/1991 | Matsumoto |
| 5,233,372 A | 8/1993 | Matsumoto |
| 5,455,644 A | 10/1995 | Yazawa et al. |
| 5,615,278 A | 3/1997 | Matsumoto |
| 5,847,805 A | 12/1998 | Kohayakawa et al. |
| 6,158,864 A | 12/2000 | Masuda et al. |
| 6,273,565 B1 | 8/2001 | Matsumoto |
| 6,327,375 B1 | 12/2001 | Matsumoto et al. |
| 6,456,787 B1 | 9/2002 | Matsumoto et al. |
| 6,488,377 B2 | 12/2002 | Matsumoto |
| 6,585,374 B2 | 7/2003 | Matsumoto |
| 6,779,890 B2 | 8/2004 | Matsumoto |
| 6,832,835 B2 | 12/2004 | Matsumoto |

(Continued)

FOREIGN PATENT DOCUMENTS

JP  2004-028970 A  1/2004

*Primary Examiner* — Jack Dinh
(74) *Attorney, Agent, or Firm* — Venable LLP

(57) ABSTRACT

Provided is an ophthalmic imaging apparatus, including: a combining unit combining return light obtained by irradiating an eye to be inspected with the measuring light, and the reference light to obtain interference light; an adjusting unit adjusting a polarization state of at least one of the return light or the reference light; and an acquiring unit acquiring information indicating depolarization of the eye using information about a difference between intensity of first interference light obtained under a first polarization state and intensity of second interference light obtained under a second polarization state, the first polarization state being in which the adjustment is performed so that polarization states of the return light and of the reference light match with each other, the second polarization state being in which the adjustment is performed so that the polarization states of the return light and of the reference light differ from each other.

9 Claims, 8 Drawing Sheets

(56) References Cited

U.S. PATENT DOCUMENTS 8,517,537 B2 8/2013 Suehira et al.
9,149,181 B2 10/2015 Matsumoto et al.
9,700,205 B2 7/2017 Yamazaki et al.

OPHTHALMIC IMAGING APPARATUS AND METHOD OF CONTROLLING THE SAME

BACKGROUND OF THE INVENTION

Field of the Invention

The present invention relates to an ophthalmic imaging apparatus, which is configured to image an eye to be inspected, and a method of controlling the ophthalmic imaging apparatus.

Description of the Related Art

A tomographic imaging apparatus (Optical Frequency Domain Imaging: OFDI), which is a type of an ophthalmic imaging apparatus configured to image an eye (for example, retina), is configured to cause return light (sample light) of measuring light reflected by the retina to interfere with reference light, and to analyze a frequency of interference fringes to generate a tomographic image. Tomographic imaging apparatus include a type using a light source configured to emit light of a wide wavelength width simultaneously, for example, an SLD light source, and a type using a swept light source (SS light source) with a periodically changing wavelength over a wide wavelength width.

Recently, there has also been developed a polarization OCT apparatus, which is configured to control polarization of the sample light, and the reference light described above to obtain polarization characteristics of an object through use of an interference intensity, a phase, and other information for each polarization component (Japanese Patent Application Laid-Open No. 2004-28970). In this manner, an orientation indicating an intensity of the polarization, a depolarization degree (DOPU) indicating a polarization maintaining amount, and other functional information can be acquired so as to know properties of the object. For example, the retinal pigment epithelium and the lamina cribrosa, which closely relate to a disease of a fundus, for example, glaucoma, form depolarization layers, and hence measuring the depolarization degree is particularly meaningful for diagnosis.

SUMMARY OF THE INVENTION

According to one embodiment of the present invention, there is provided an ophthalmic imaging apparatus, including: a combining unit, which is configured to combine, after light emitted from a light source is divided into measuring light and reference light, return light, which is obtained by irradiating an eye to be inspected with the measuring light, and the reference light to obtain interference light; an adjusting unit, which is configured to adjust a polarization state of at least one of the return light or the reference light; and an acquiring unit, which is configured to acquire information indicating depolarization of the eye to be inspected using information about a difference between intensity of first interference light obtained under a first polarization state and intensity of second interference light obtained under a second polarization state, the first polarization state being in which the adjustment is performed so that a polarization state of the return light and a polarization state of the reference light match with each other, the second polarization state being in which the adjustment is performed so that the polarization state of the return light and the polarization state of the reference light differ from each other.

According to another embodiment of the present invention, there is provided an ophthalmic imaging apparatus, including: a combining unit, which is configured to combine, after light emitted from a light source is divided into measuring light and reference light, return light, which is obtained by irradiating an eye to be inspected with the measuring light, and the reference light to obtain interference light; an adjusting unit, which is configured to adjust a polarization state of at least one of the return light or the reference light; and as acquiring unit, which is configured to acquire information on depolarization of the eye to be inspected through use of an intensity of first interference light, which is obtained when a polarization state of the return light and a polarization state of the reference light are in a first relationship, and an intensity of second interference light, which is obtained when a matching degree between the polarization state of the return light and the polarization state of the reference light is adjusted to establish a second relationship, which is different in matching degree from the first relationship.

According to still another embodiment of the present invention, there is provided a method of controlling the above-mentioned ophthalmic imaging apparatus.

Further features of the present invention will become apparent from the following description of exemplary embodiments with reference to the attached drawings.

DESCRIPTION OF THE EMBODIMENTS

Preferred embodiments of the present invention will now be described in detail in accordance with the accompanying drawings.

In a related-art polarization OCT apparatus, in order to solve a determinant of polarization to determine polarization components (Stokes parameters), a large amount of data on different polarization states is required. More specifically, in order to obtain the large amount of data on the different polarization states, the related-art polarization OCT apparatus is required to include a large number of optical members (for example, polarizer and respective wave plates) relating to polarization, and there have been problems in that a configuration of the apparatus is complicated, and that processing performed by the apparatus is also complicated. Therefore, imaging takes much time, and a plurality of sets of data obtained by imaging the same site are required for providing polarization information on the same site, with the result that the imaging has been difficult in some cases. Exemplary embodiments of the present invention have been devised in view of the above-mentioned problems, and therefore have an object to provide a mechanism capable of acquiring information indicating depolarization of an eye to be inspected with simple configuration and processing.

Modes for carrying out the present invention (embodiments of the present invention) are described below referring to the accompanying drawings.

First Embodiment

First, a first embodiment of the present invention is described.

Apparatus Configuration

Figure 1:
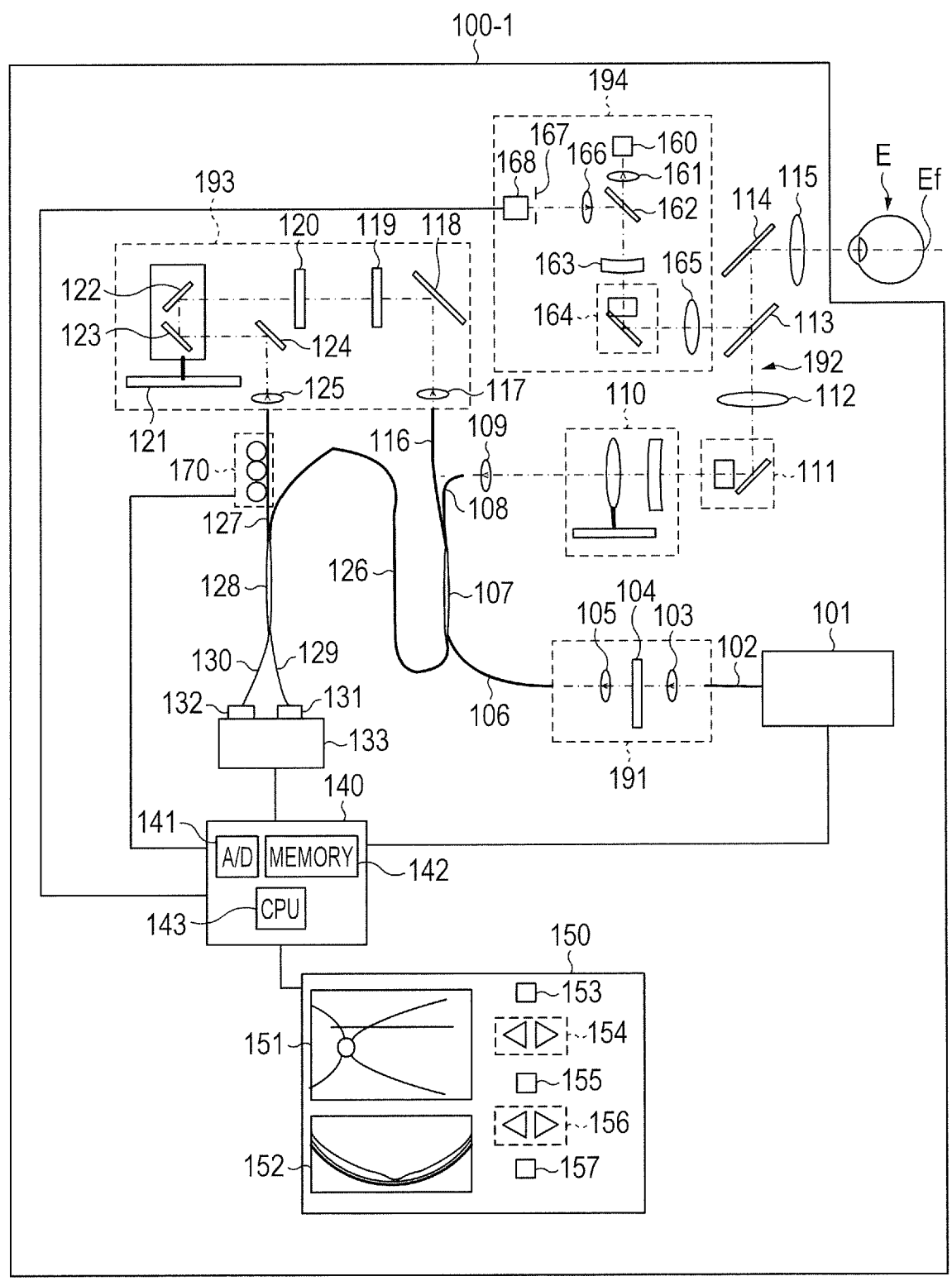
FIG. 1 is a diagram for illustrating an example of a schematic configuration of an ophthalmic imaging apparatus according to a first embodiment of the present invention.

FIG. 1 is a diagram for illustrating an example of a schematic configuration of an ophthalmic imaging apparatus 100 according to the first embodiment of the present invention. This ophthalmic imaging apparatus 100 is an apparatus configured to acquire an image of a retina (fundus Ef), an anterior segment, or another area of an eye E to be inspected, for example. In the following description, an example of imaging the fundus Ef of the eye E to be inspected is described. Moreover, in the following description, there is described an example in which an apparatus configured to imago the eye E to be inspected through use of Fourier domain optical coherence tomography is applied as the ophthalmic imaging apparatus 100. Moreover, the ophthalmic imaging apparatus 100 illustrated in FIG. 1 is referred to as "ophthalmic imaging apparatus 100-1".

An OCT light source 101 is a light source configured to generate low coherence light. In the first embodiment, as the OCT light source 101, an SS (swept) light source having a center wavelength of about 1,060 nm and a swept wavelength width of about 100 nm is used, for example. In this case, the SS light source, which is a light source configured to emit light of a wavelength that is changed at certain intervals, emits light having a wavelength that is changed within a wavelength width of about 100 nm at a predetermined frequency of from about 100 kHz to about 300 kHz.

The light emitted from the OCT light source 101 is guided to a light control unit 191 through a fiber 102. The light control unit 191 includes a collimator lens 103, a neutral-density filter (ND filter) 104 having a variable transmittance, and a collimator lens 105. Light that has exited the light control unit 191 is guided to a light dividing unit 107 through a fiber 106. The light dividing unit 107 is a dividing unit configured to divide light that has exited the OCT light source 101 into measuring light and reference light. In the following description, return light obtained when the measuring light with which the ophthalmic imaging apparatus 100-1 irradiates the eye E to be inspected is reflected by the eye E to be inspected (specifically, fundus Ef) and returns to the ophthalmic imaging apparatus 100-1 is described as "sample light". As the light dividing unit 107, it is conceivable to employ a prism beam splitter or a planar beam splitter, for example, but in the first embodiment, a light dividing unit of a fiber coupler type is used. Moreover, an appropriate ratio of division performed by the light dividing unit 107 can be selected in consideration of output from the OCT light source 101, an amount of light emitted to the eye E to be inspected, which serves as an object, and other such factors. In the first embodiment, the ratio of division performed by the light dividing unit 107 is 10% on the sample light side (measuring light side) and 90% on the reference light side.

Light that has been branched off to a fiber 108 on the sample light side (measuring light side) by the light dividing unit 107 is guided to a sample optical system 192. The sample optical system 132 includes a collimator lens 109, a focus adjusting unit 110, an optical scanning member 111, a relay lens 112, a dividing mirror 113, a mirror 114, and an objective lens 115. The optical scanning member 111 is arranged to be substantially conjugate to a pupil position of the eye E to be inspected so as to combine main scan and sub scan to two-dimensionally scan a light beam over the retina (fundus Ef) of the eye to be inspected. As the optical scanning member 111, a pair of galvanometer mirrors, which are arranged adjacent to each other in an optical axis direction (arranged in tandem), and are configured to scan light in an x direction and a y direction that are orthogonal to each other, are employed, for example. In this manner, the light that has been transmitted through the light dividing unit 107 reaches the fundus Ef of the eye E to be inspected through the sample optical system 192.

Moreover, light that has been branched off to a fiber 116 on the reference light side by the light dividing unit 107 is guided to a reference optical system 193. The reference optical system 193 includes a collimator lens 117, a mirror 118, an ND filter 119 configured to adjust an amount of light, a transmittance correction filter 120 having a transmittance different depending on a wavelength, mirrors 122 and 123 arranged on a movable stage 121 to adjust an optical path length, a mirror 124, and a condenser lens 125. A fiber 127 is arranged beyond the condenser lens 125, and a polarization adjusting unit 170 is mounted on the fiber 127. The polarization adjusting unit 170 is configured to be able to perform adjustment so that a polarization state of the reference light of the reference optical system 193 is changeable, and to be able to control an intensity of interference with the sample light of the sample optical system 192.

The measuring light that has been reflected by the eye E to be inspected returns as the sample light to the fiber 108 through the sample optical system 192, and 90% of the light is branched off to a fiber 126 by the light dividing unit 107 to enter a fiber coupler 128.

The reference light from the reference optical system 103 also enters the fiber coupler 128 through the fiber 127. The fiber coupler 128 is a combining unit configured to combine the sample light and the reference light that have entered the fiber coupler 128 to obtain interference light. Then, the interference light is divided at 50:50 into light with inverted interference phases by the fiber coupler 128, and the divided light is input to input terminals 131 and 132 of a differential sensor 133 through fibers 129 and 130, respectively, to be converted into an electrical signal (interference signal) by the differential sensor 133.

A controller 140 is configured to perform various kinds of control and various kinds of processing, and includes an A/D converter 141, a memory 142, and a CPU 143. The A/D converter 141 is configured to convert the analog electrical signal (interference signal) obtained by the differential sensor 133 into a digital electrical signal (interference signal). The memory 142 has stored therein various kinds of information, data, and programs, which are required when the controller 140 performs the various kinds of control and the various kinds of processing, for example, and is configured to store various kinds of information and data obtained when the controller 140 performs the various kinds of processing. For example, the memory 142 is configured to store data relating to the digital electrical signal (interference signal) obtained by the A/D converter 141. The CPU 143 is configured to perform the various kinds of control and the various kinds of processing. For example, the CPU 143 computes the data relating to the electrical signal (interference signal) stored in the memory 142, structures tomographic image data, and performs control of displaying, on a tomographic image display area 152 of a display 150, a tomographic image obtained by using the tomographic image data.

Moreover, on a reflection optical path of the dividing mirror 113, an SLO unit 194 is arranged. The SLO unit 194 includes an SLO light source 160, a collimator lens 161, a perforated mirror 162 configured to divide light into projection light and return light, a focus lens 163, a scanning member 164, and a relay lens 165. The SLO light source 160 is a light source configured to emit near-infrared light of about 780 nm, for example. The scanning member 164 is a scanning member, which includes a resonant mirror and a galvanometer mirror arranged in proximity to each other, and is configured to be able to two-dimensionally scan the fundus Ef. Moreover, on a reflection optical path of the perforated mirror 162, a condenser lens 166, a confocal diaphragm 167, and a light receiver 168, for example, an APD, are provided. Then, as in the case of the tomographic image described above, the controller 140 structures SLO image data relating to an electrical signal obtained by the light receiver 168, and performs control of displaying, on an SLO image display area 151 of the display 150, an SLO image obtained by using the SLO image data.

Imaging Method

Next, there is described a method of acquiring the tomographic image of the retina of the fundus Ef of the eye E to be inspected through use of the ophthalmic imaging apparatus 100-1 illustrated in FIG. 1.

The eye E to be inspected is placed in front of the ophthalmic imaging apparatus 100-1. An imaging person first observes the fundus Ef of the eye E to be inspected through use of the SLO unit 194 to adjust an appropriate working distance (WD), confirm a site to be imaged, and performs focus adjustment. In other words, when the imaging person operates a switch 153 on the display 150, the CPU 143 starts an SLO imaging mode. When the SLO imaging mode is started, the CPU 143 lights up the SLO light source 160. SLO light emitted from the SLO light source 160 exits the SLO unit 194, and is reflected by the dividing mirror 113 to a direction of the eye E to be inspected to enter the fundus Ef of the eye E to be inspected through the objective lens 115. The dividing mirror 113 reflects light of about 780 nm, which is a wavelength of the SLO light source 160, and transmits most of light in a 1,000-nm band, which is used to acquire the tomographic image. Then, the SLO light reflected by the eye E to be inspected follows the optical path backwards to enter the SLO unit 194 again, and is reflected by a peripheral portion of the perforated mirror 162 to be received by the light receiver 168 via the confocal diaphragm 167 and converted into the electrical signal. The electrical signal is sent to the controller 140. In the controller 140, the electrical signal is converted into a digital signal by the A/D converter 141 to be stored in the memory 142, and is converted into the SLO image data to be displayed in the SLO image display area 151 on the display 150.

The imaging person adjusts a working distance between the objective lens 115 and the eye E to be inspected and decentering through use of an operation unit (not shown) while observing the SLO image displayed on the display 150 so that a fundus image is seen clearly in the entire area of the display area. Further, the imaging person operates a focus adjustment button 154 to adjust focus so that a contrast of the image is seen clearly. A signal from the focus adjustment button 154 moves the focus lens 163 of the SLO unit 194 in the optical axis direction, and also moves a lens of the focus adjusting unit 110 of the sample optical system 192 in the optical axis direction. In this manner, the SLO optical system and the OCT optical system are always maintained at the same diopter.

After confirming that the working distance between the objective lens 115 and the eye to be inspected, and the focus are appropriate through the SLO image, the imaging person operates a switch 155 to change the mode to an OCT preview mode. After the change to the OCT preview mode, the controller 140 lights up the OCT light source 101 to start wavelength sweeping. The light emitted from the OCT light source 101 is adjusted to have an appropriate amount of light by the ND filter 104 in the light control unit 191. Then, 90% of the light is branched off to the reference light side, and 10% of the light is branched off to the sample light side by the light dividing unit 107. The measuring light branched off to the sample light side enters the sample optical system 192, and is scanned by the focus adjusting unit 110 that has finished the focus adjustment and the optical scanning member 111 to enter the fundus Ef of the eye E to be inspected. Light reflected and scattered by each layer boundary surface of the retina of the eye to be inspected follows the original optical path backwards to enter the light dividing unit 107 through the fiber 108.

Meanwhile, the reference light branched off to the reference light side by the light dividing unit 107 enters the reference optical system 193, and is adjusted to have an appropriate amount of light by the ND filter 119 configured to adjust an amount of reference light. After that, the reference light is corrected in spectral intensity distribution by the transmittance correction filter 120, and is collected by the fiber 127 to enter the 50:50 fiber coupler 128 for interference. The reference light and the sample light being the return light, which have entered the fiber coupler 128, interfere with each other to be the interference light. The interference light is divided at a ratio of 50:50 into light with inverted phases to enter the differential sensor 133, and an interference component, which is a difference therebetween, is converted into an electrical signal (interference signal), which is input to the controller 140.

The electrical signal (interference signal) is converted into digital data by the A/D converter 141, stored in the memory 142, and then subjected to wave number conversion, Fourier transform, and other processing by the CPU 143 to generate the tomographic image. The generated tomographic image is displayed in the tomographic image display area 152 of the display 150. The imaging person observes the tomographic image, and adjusts the optical path length of the reference optical system 193 again through use of an alignment adjustment button 156 so that a desired site to be imaged enters an imaged area. The CPU 143 that has detected input to the alignment adjustment button 156 controls the movable stage 121 to move the mirrors 122 and 123, to thereby adjust the optical path length of the reference optical system 193. The imaging person who has confirmed that OCT imaging is being performed appropriately through the above-mentioned operation operates an imaging switch 157. The CPU that has detected input to the imaging switch 157 acquires a predetermined number of, namely, 50 to 150, OCT images of the same site, displays a tomographic image obtained by superimposing the OCT images on one another in the tomographic image display area 152, and ends imaging under a strong interference state.

Control of Polarization Adjusting Paddles

Next, control of polarization is described.

Figure 2:
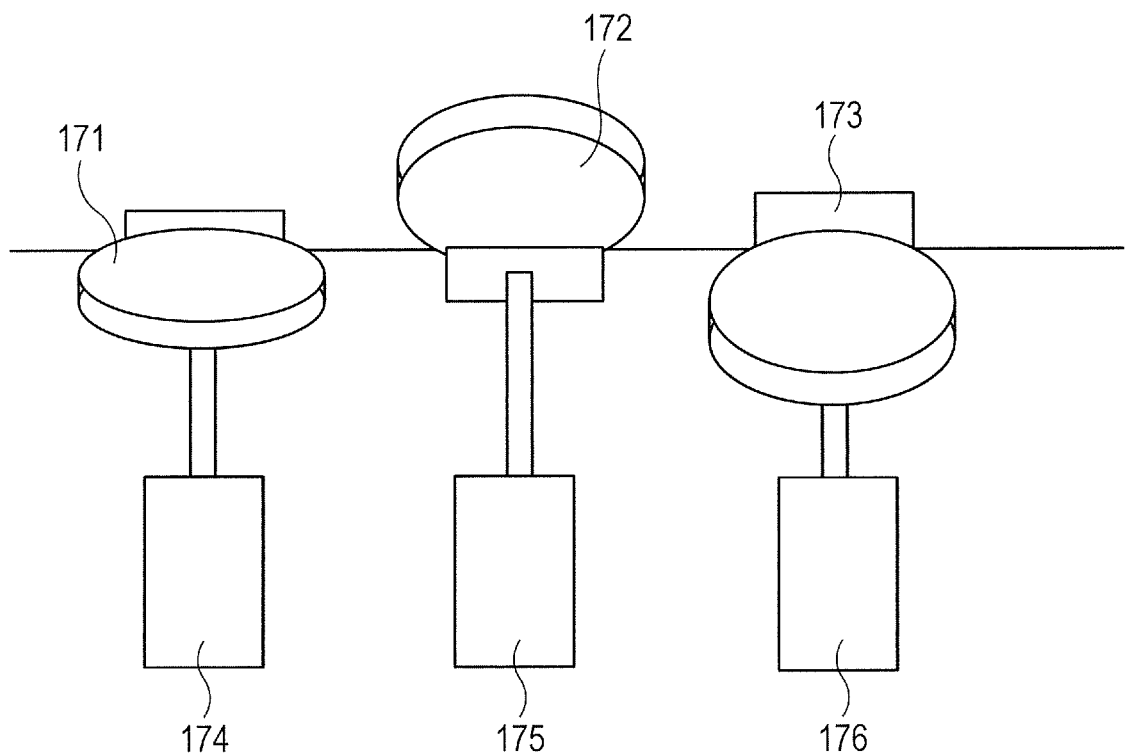
FIG. 2 is a diagram for illustrating an example of a schematic configuration of a polarization adjusting unit illustrated in FIG. 1.

FIG. 2 is a diagram for illustrating an example of a schematic configuration of the polarization adjusting unit 170 illustrated in FIG. 1. As illustrated in FIG. 2, the polarization adjusting unit 170 includes a plurality of paddles 171 to 173, and a plurality of stepping motors 174 to 176 provided to correspond to the plurality of paddles 171 to 173, respectively.

Specifically, a fiber is wound around each of the paddles 171 to 173, and the three paddles are configured to be independently adjustable in angle with a straight axis of the fiber entering the paddle being an axis of rotation. Those paddles 171, 172, and 173 are configured to be adjustable in angle by the stepping motors 174, 175, and 176, respectively. An angle of each of the paddles 171 to 173 is adjustable from −90° to +90°. In this case, 0° is a direction perpendicular to the drawing sheet. The angles of the paddles 171 to 173 can be adjusted to adjust a polarization state of light that has passed through the paddles 171 to 173. For example, a single mode fiber generates birefringence by being bent. Therefore, an amount of birefringence generated by each of the paddles 171 to 173 is determined by a curvature radius of the paddle around which the fiber is wound and the number of turns of the fiber, and can be calculated by the following expression (1).

$$\Phi(Waves)=naNd^2/\lambda D \quad (1)$$

where $\Phi$ represents an amount of birefringence (retardance), a represents a constant (0.133 for silica fiber), N represents the number of turns of the fiber, d represents a clad diameter of the fiber, $\lambda$ represents a wavelength of light, and D represents a curvature radius of the paddle.

The adjustment is performed efficiently when the curvature radius D of the paddle and the number N of turns of the fiber are set so that an amount of birefringence generated by the paddle 171 is $\lambda/4$, an amount of birefringence generated by the paddle 172 is $\lambda/2$, and an amount of birefringence generated by the paddle 173 is $\lambda/4$. However, this is merely an example, and the above-mentioned amounts of birefringence are not necessarily required to be set as long as the three paddles 171 to 173 are moved so that a freely-selected polarization state can be set. However, in the first embodiment, the configuration with which the above-mentioned amounts of birefringence are generated is adopted.

Polarization Adjustment and Interference Intensity

FIG. 3A to FIG. 3D are charts for showing the first embodiment of the present invention, in which examples of a polarization state of the sample light and polarization states of the reference light are shown.

Figure 3A:
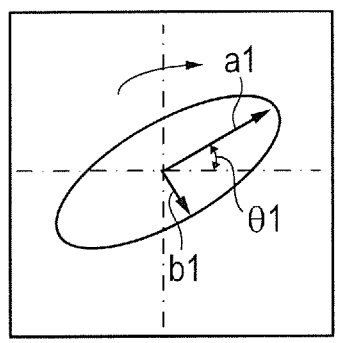
FIG. 3A, FIG. 3B, FIG. 3C, and FIG. 3D are charts for showing the first embodiment, in which examples of a polarization state of sample light and polarization states of reference light are shown, respectively.
Figure 3B:
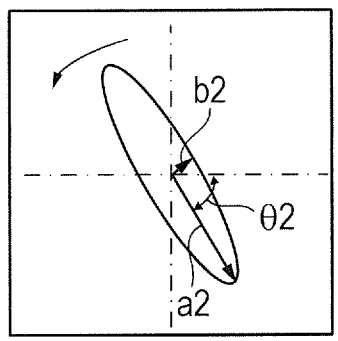
Figure 3C:
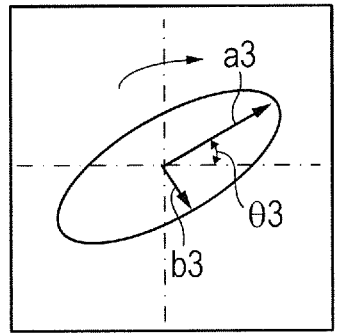
Figure 3D:
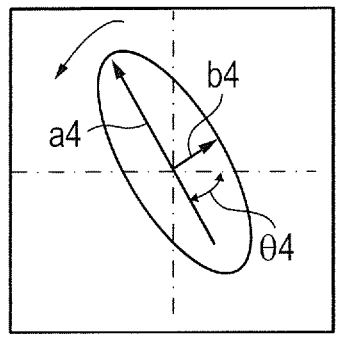
Figure 4:
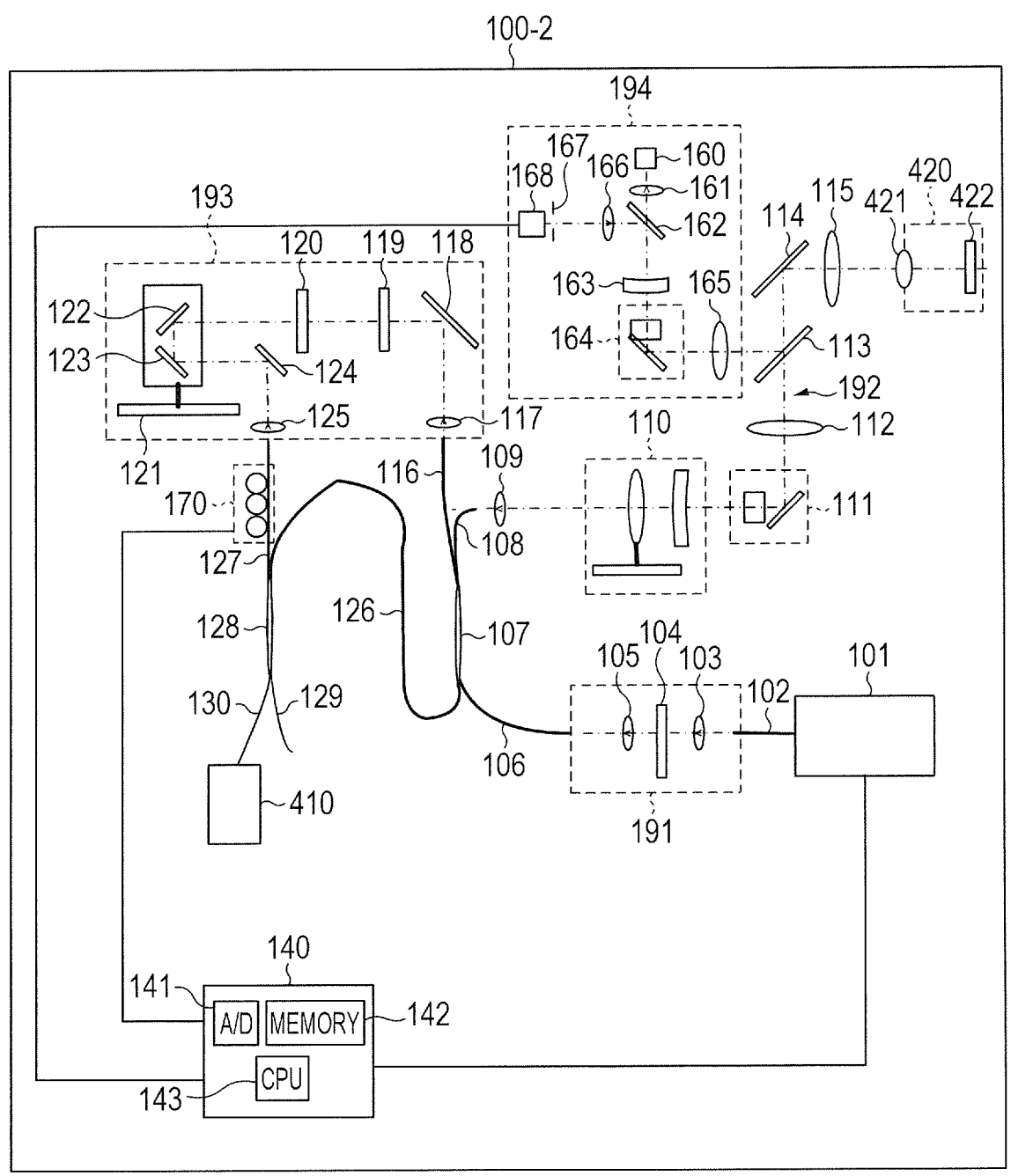
FIG. 4 is a diagram for illustrating the first embodiment, in which an example of a schematic configuration of the ophthalmic imaging apparatus at a time of measuring the polarization states shown in FIG. 3A to FIG. 3D is illustrated.

Moreover, FIG. 4 is a diagram for illustrating the first embodiments of the present invention, in which an example of a schematic configuration of the ophthalmic imaging apparatus 100 at a time of measuring the polarization states shown in FIG. 3A to FIG. 3D is illustrated. In FIG. 4, components similar to those illustrated in FIG. 1 are denoted by the same reference symbols, and the ophthalmic imaging apparatus 100 illustrated in FIG. 4 is referred to as "ophthalmic imaging apparatus 100-2".

To a polarization meter 410 illustrated in FIG. 4, the fiber 130, which is one of output fibers of the fiber coupler 128, is connected. The polarization meter 410 is capable of measuring an azimuth angle ($\Phi$), an ellipticity ($\eta$), and right-handed polarization or left-handed polarization, which are polarization components of input light. A tool 420 is a tool configured to measure polarization, and includes a lens 421 and a mirror 422. The mirror 422 is arranged substantially at a focal plane of the lens 421. The tool 420 is mounted to the objective lens 115, and the optical scanning member 111 is controlled to adjust an angle of incidence on the mirror 422 and is fixed at the adjusted angle so that light that has exited the objective lens 115 is reflected to be returned to the objective lens 115.

With such arrangement, the polarization, state of the sample light of the sample optical system 192 is measured first. At this time, in order to block the reference light, the ND filter 119 in the reference optical system 193 is controlled to block the reference light. The light emitted from the OCT light source 101 travels a path similar to that in the case described above with reference to FIG. 1, is reflected by the mirror 422 of the tool 420, follows the same optical path as the forward path backwards to return to the fiber coupler 128, and enters the polarization meter 410 through the fiber 130 so that the polarization state is measured. Polarization characteristics are different depending on the wavelength, and hence the measured wavelength may be limited through use of a bandpass filter having a wavelength width of from about 1 nm to about 2 nm. In the first embodiment, a bandpass filter having a transmitted wavelength of 850 nm and a full width at half maximum of 2 nm is used.

FIG. 3A is a chart for showing an example of a measurement result under the polarization state of the sample light. In FIG. 3A, the polarization characteristics are expressed by the following parameters; an azimuth angle represented by $\theta 1$ and art eilipticity represented by $\eta=a \tan(b1/a1)$, where $\eta>0$ means right-handed polarization, $\eta<0$ means left-handed polarization, and $\eta=0$ means linear polarization.

Next, the polarization state or the reference system of the reference optical system 193 is measured. At this time, in order to measure only the reference light of the reference optical system 133, the angle of the optical scanning member 111 is controlled to divert the sample light from the optical path, to thereby achieve a state in which no light enters from the sample optical system 192. Then, the ND filter 119 in the reference optical system 193 is set at a light transmitting position. As a result, the polarization characteristics of the reference light can be measured.

In this case, it is assumed that a measurement result under the polarization state of the reference light is that shown in FIG. 3B. In other words, it is assumed that an azimuth angle is $\theta 2$, and an ellipticity is $\eta=a \tan(b2/a2)$. Under this state, the polarization state of the sample light shown in FIG. 3A and the polarization state of the reference light shown in FIG. 3B do not match, and the interference signal is weak. Then, the controller 140 controls the stepping motors 174 to 176 to adjust the angles of the paddles 171 to 173 of the polarization adjusting unit 170, to thereby perform polarization adjustment. As described above, when the amount of birefringence of the paddle 171 is set to λ/4, the angle of the paddle 171 can be adjusted to adjust the polarization state to linear polarization (ellipticity: 0°). Further, the angle of the paddle 172 is adjusted to be equal to the azimuth angle θ1 of the sample light. Further, the angle of the paddle 173 is adjusted so that the ellipticity is equal to that of the sample light. As a result, as shown in FIG. 3C, the polarization state of the reference light can be adjusted to match with the polarization state of the sample light shown in FIG. 3A. Therefore, in this case, the sample light and the reference light strongly interfere with each other, and a point spread function (PSF) obtained by subjecting an interference waveform to Fourier transform also exhibits a high value with a narrow fall width at half maximum. Then, the CPU 143 stores, in the memory 142, driving values (Stmax1, Stmax2, and Stmax3) of the stepping motors 174, 175, and 176 corresponding to thus-adjusted angles (θa1, θb1, and θc1) of the paddles 171, 172, and 173, respectively.

Next, angles of the paddles 171 to 173 that provide a noninterference state are set. The polarization state of the reference light that most strongly interferes with the polarization state of the sample light shown in FIG. 3A is a polarization state of FIG. 3C, which is the same as that of FIG. 3A. In other words, the azimuth angle θ1=θ3, and an ellipticity η=a tan(b1/a1)=a tan(b3/a3). In contrast, the polarization state of the reference light that most weakly interferes with the polarization state of the sample light shown in FIG. 3A is a polarization state of FIG. 3D, in which a polarization state opposite to that of FIG. 3A (state that is completely opposite on the Poincare sphere) is shown. In other words, the polarization state of FIG. 3D is a state in which an ellipticity is equal to that of the polarization state of FIG. 3A, and an azimuth angle is different from that of the polarization state of FIG. 3A by 90° (ellipticity η=a tan(b4/a4)=−a tan(b1/a1) and θ4=θ1−90°. Then, the CPU 143 determines angles (θa2, θb2, and θc2) of the respective paddles 171, 172, and 173 that are adjusted so that the polarization state of the reference light equals to that of FIG. 3D, and stores, in the memory 142, the driving values (Stmin1, Stmin2, and Stmin3) of the stepping motors 174, 175, and 176 corresponding to those angles, respectively. When the adjustment values are obtained as described above, the polarization meter 410 and the tool 420 are removed, and the fibers 129 and 130 are connected to the differential sensor 133.

Acquisition of Information Indicating Depolarization

First, the controller 140 performs normal OCT imaging on the eye E to be inspected (specifically, fundus Ef) with the paddle angles (θa1, θb1, and θc1) under the interference state to generate the tomographic image data (OCT image data). The OCT imaging here is imaging under a first polarization state in which the controller 140 controls the polarization adjusting unit 170 so that the polarization state of the sample light and the polarization state of the reference light match with each other, and the OCT image data obtained through the imaging corresponds to first image data (hereinafter referred to as "first OCT image data").

Next, the controller 140 drives the stepping motors 174, 175, and 176 with the values (Stmin1, Stmin2, and Stmin3) stored in the memory 142, and performs the OCT imaging with the paddle angles (θa2, θb2, and θc2) under the noninterferences state to generate OCT image data. The OCT imaging here is imaging under a second polarization state in which the controller 140 controls the polarization adjusting unit 170 such that the polarization state of the sample light and the polarization state of the reference light differ from each other, and the OCT image data obtained through the imaging corresponds to second image data (hereinafter referred to as "second OCT image data").

The above-mentioned first polarization state means a case in which the polarization state of the return light and the polarization state of the reference light are in a first relationship. Meanwhile, the above-mentioned second polarization state means a case in which the polarization state of the return light and the polarization state of the reference light are in a second relationship, which is different in matching degree from the first relationship. In the first relationship, it is preferred that the adjustment be performed so that the polarization state of the return light and the polarization state of the reference light match with each other, but the polarization state of the return light and the polarization state of the reference light are not necessarily required to completely match with each other as long as information on depolarization of the eye E to be inspected can be acquired through use of two relationships. Moreover, as compared to the first relationship, in the second relationship, the polarization adjusting unit 170, which is an adjusting unit, performs the adjustment so that the matching degree between the polarization state of the return light and the polarization state of the reference light is low, for example.

In this case, in the first embodiment, through the imaging under the first polarization state and the imaging under the second polarization state described above, there is acquired an OCT image that does not interfere with a signal from a target in which polarization is maintained (hereinafter referred to as "depolarization OCT imaging").

For example, the CPU 143 performs processing of acquiring the information indicating the depolarization of the eye to be inspected using information about a difference between intensity of first interference light obtained under the above-mentioned first polarization state, and intensity of second interference light obtained under the second polarization state. Specifically, the CPU 143 acquires, through use of the above-mentioned first OCT image data and the above-mentioned second OCT image data, which are expressed by pixel values using the intensities of the interference light, an image (third image data) indicating the depolarization as the information indicating the depolarization. More specifically, in the first embodiment, when the first OCT image data is expressed as I_max(x,z), and the second OCT image data is expressed aa I_min(x,z), the CPU 143 acquires image data I_np(x,z) indicating the depolarization by performing subtraction expressed by the following expression (2):

$$I\_np(x,z)=I\_\max(x,z))-I\_\min(x,z)) \qquad (2).$$

In the expression (2), x represents a coordinate in a main scanning direction, and s represents a coordinate in a depth direction of the eye E to be inspected.

When the imaging is performed with the combination of paddle angles under the interference state, the interference signal from a layer in which polarization of reflected and scattered light is maintained with respect to incident light is strong, end the interference signal from a layer with a large difference in polarization of the reflected and scattered light with respect to the incident light is weak. In contrast, in the case of the depolarization OCT imaging, the interference signal from a site in which the polarization is maintained is weak, while the interference signal from a site in which the difference in polarization is large is strong. In other words, in the case of the depolarization OCT imaging, there can be obtained the tomographic image in which the nerve fiber layer, the lamina cribrosa, the retinal pigment epithelium, a tissue in which fibrosis has progressed, and other depolarization sites of the eye E to be inspected are highlighted, for example.

Then, with the use of the image data indicating the depolarization obtained by the depolarization OCT imaging, diagnosis of the depolarization sites is facilitated. Further, by using both of the first OCT image data and the second OCT image data, accuracy of layer segmentation can be improved. In other words, a layer boundary between a polarization maintaining layer and a depolarization layer is clearly shown in the image data indicating the depolarization. Therefore, information on the layer boundary is determined from the image data indicating the depolarization, and the other layer boundaries are determined from normal OCT image data (for example, first OCT image data), to thereby be able to improve the accuracy of segmentation.

Second Embodiment

Next, a second embodiment of the present invention is described.

A schematic configuration of an ophthalmic imaging apparatus 100 according to the second embodiment is similar to that of the ophthalmic imaging apparatus 100 (ophthalmic imaging apparatus 100-1) according to the first embodiment illustrated in FIG. 1. In the following description of the second embodiment, differences from the first embodiment are described.

Polarization Adjustment Using PSF

In the first embodiment, the example in which the combination of paddle angles under the interference state and the combination of paddle angles under the noninterference state are used to perform the polarization adjustment through use of the polarization meter 410 has been described. In the second embodiment, there is described an example in which a PSF obtained by performing the Fourier transform on the interference signal between the sample light being the return light from the tool 420 arranged in the sample optical system 192 and the reference light of the reference optical system 193 is used to perform the polarization adjustment of the paddle angles.

Figure 5:
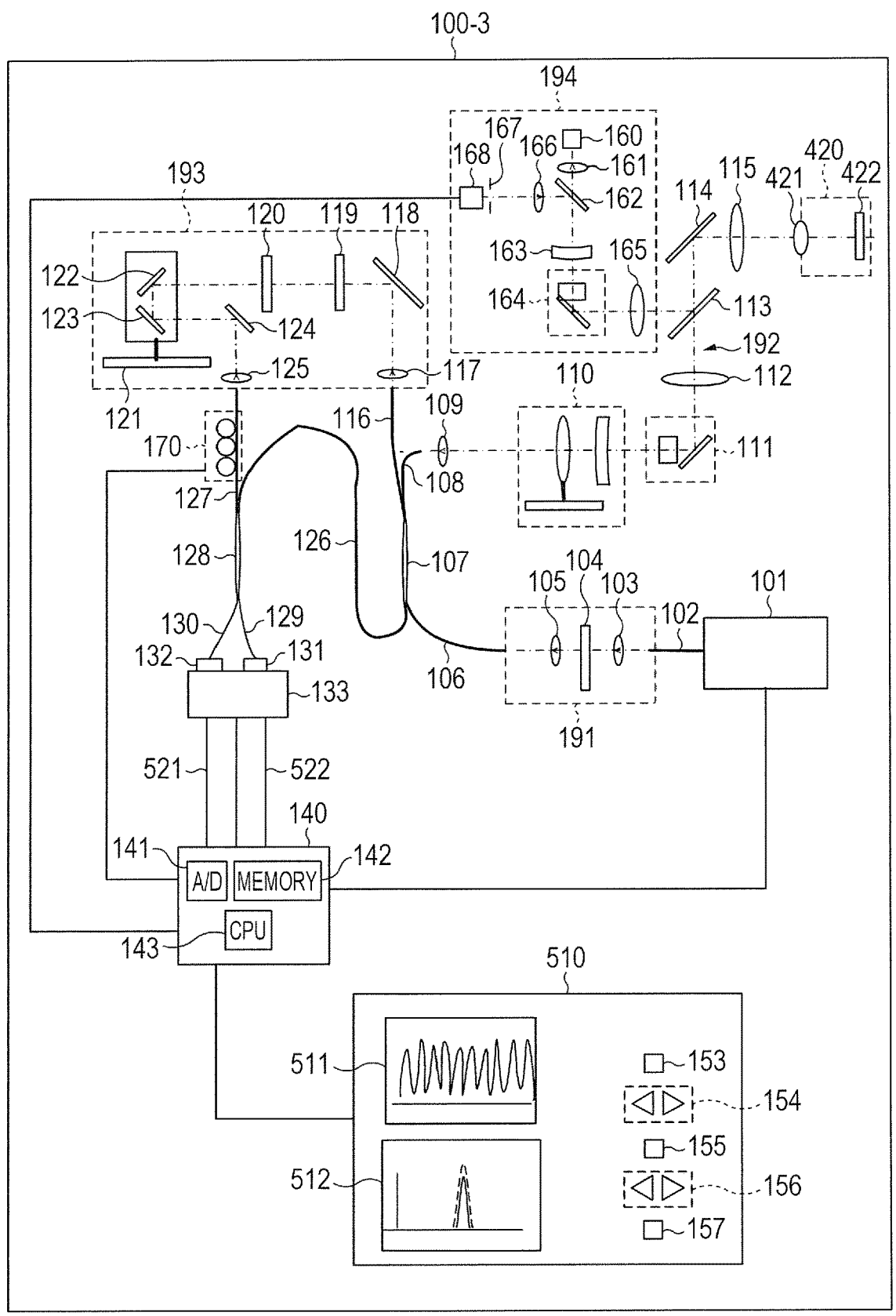
FIG. 5 is a diagram for illustrating a second embodiment of the present invention, in which an example of a schematic configuration of an ophthalmic imaging apparatus at a time of measuring (adjusting) a polarization state is illustrated.

FIG. 5 is a diagram for illustrating the second embodiment of the present invention, in which an example of a schematic configuration of the ophthalmic imaging apparatus 100 at a time of measuring (adjusting) the polarization state is illustrated. In FIG. 5, components similar to those illustrated in FIG. 4 are denoted by the same reference symbols, and the ophthalmic imaging apparatus 100 illustrated in FIG. 5 is referred to as "ophthalmic imaging apparatus 100-3".

When the ophthalmic imaging apparatus 100-3 is booted in a paddle adjustment mode, the interference signal is displayed in a display area 511 of a display 510, and a PSF obtained by subjecting the interference signal to the Fourier transform is displayed in a display area 512 of the display 510. At this time, the optical scanning member 111 is at rest under a state in which light returns efficiently from the mirror 422 of the tool 420, the ND filter 119 is in a light transmission state, and a C-gate is arranged at a position at which a difference in optical path length between the reference optical system 193 and the sample optical system 192 is several tens of µm, to thereby generate low-frequency interference fringes, for example.

Figure 6:
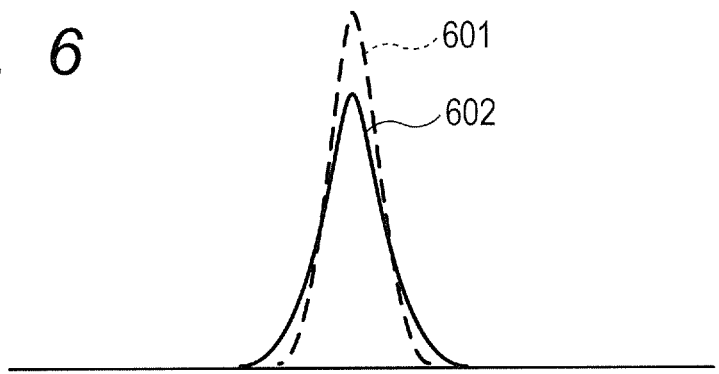
FIG. 6 is a graph for showing an example of a PSF displayed in a display area illustrated in FIG. 5.

FIG. 6 is a graph for showing an example of the PSF displayed in the display area 512 illustrated in FIG. 5.

In FIG. 6, a broken line 601 indicates a PSF of an ideal interference waveform calculated by using the spectral intensity distribution, and a solid line 602 indicates a PSF calculated by using an actual interference waveform. In this case, a ratio of a height of the solid line 602 to a height of the broken line 601 is referred to as a "PL value". The PL value corresponds to a matching degree value indicating a matching degree between the polarization state of the sample light and the polarization state of the reference light. Moreover, the PL value is calculated by the CPU 143, for example. When the differential sensor 133 is used, the signal regarding the spectral intensity distribution is lost by the subtraction, and hence is obtained by using monitoring signals 521 and 522 before the subtraction.

Figure 7:
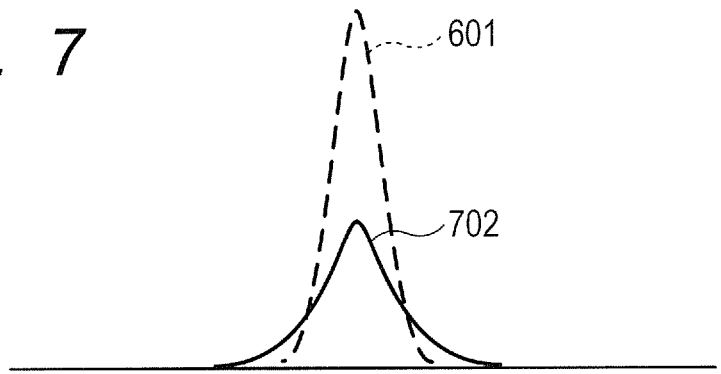
FIG. 7 is a graph for showing another example of the PSF displayed in the display area illustrated in FIG. 5.
Figure 8:
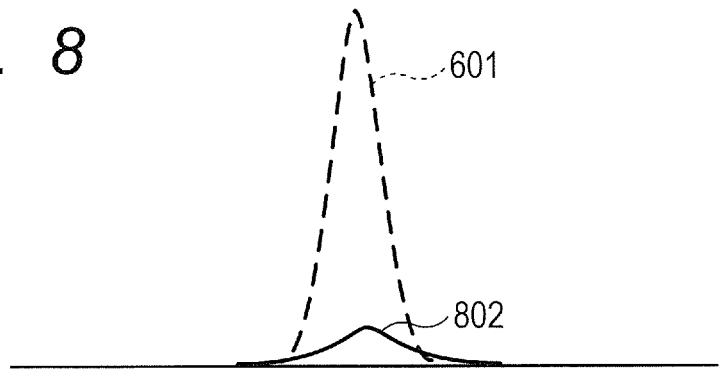
FIG. 8 is a graph for showing still another example of the PSF displayed in the display area illustrated in FIG. 5.

In this case, when the polarization state of the sample light of the sample optical system 192 and the polarization state of the reference light of the reference optical system 193 completely match with each other, the ideal interference waveform is obtained, and hence the PL value is 1.0. Moreover, when the angles of the paddles are adjusted to change the polarization state of the reference light, an interference intensity is reduced as indicated by a solid line 702 shown in FIG. 7 to exhibit a state in which the PL value is low. Further, the polarization state of the reference light may be adjusted so that the PL value is 0.1 or less as indicated by a solid line 802 shown in FIG. 8. In reality, however, a wavelength width of light used in the OCT is wide, and the polarization characteristics are different depending on the wavelength. Therefore, it is difficult to create a state in which the polarizations completely match with each other in all wavelength bands (PL value=1), or a state in which the polarizations are completely orthogonal to each other in all wavelength bands (PL value=0). Therefore, similar effects are obtained also by storing, in the memory 142, values ($\theta a1$, $\theta b1$, $\theta c1$, and PL1) indicating the combination of paddle angles at a time when a PL value is the highest and the PL value PL1 at the time, and values ($\theta a2$, $\theta b2$, $\theta c2$, and PL2) indicating the combination of paddle angles at a time when the PL value is the lowest and a PL value PL2 at the time, and performing the OCT imaging with the paddle angles.

Figure 9:
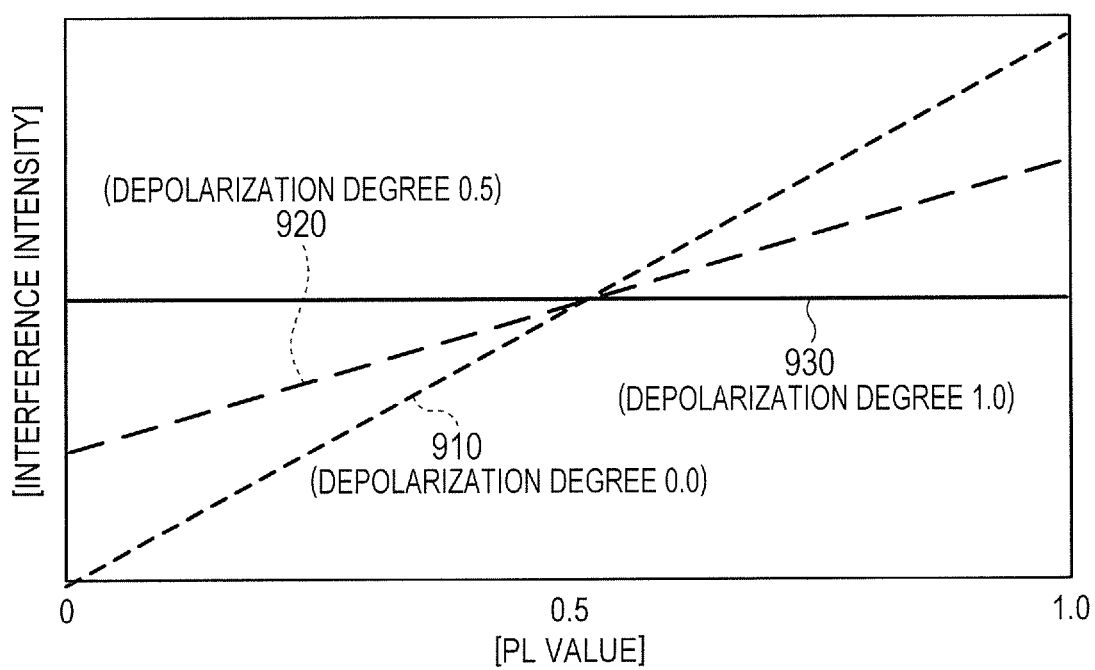
FIG. 9 is a conceptual graph for showing the second embodiment, in which an example of a relationship between a PL value and an interference intensity is shown.

FIG. 9 is a conceptual graph for showing the second embodiment of the present invention, in which an example of a relationship between the PL value and the interference intensity is shown. When intensities of the reflected and scattered light from the object are assumed to be equal, a signal from the object completely maintaining the polarization (depolarization degree: 0.0) has the interference intensity of 0 when the PL value is 0, and has the strongest interference intensity when the PL value is 1. When the depolarization degree of the object is 1.0, that is, polarization components of the reflected and scattered light with respect to the incident polarization are completely uniform, the interference intensity is unchanged even when the PL value is changed. When the depolarization degree is 0.5, the interference intensity exhibits an intermediate result. In other words, when the PL value is taken on the horizontal axis, and the interference intensity is taken on the vertical axis as shown in FIG. 9, a slope of the graph corresponds to the depolarization degree. Therefore, the adjustment is not necessarily required to be performed such that the PL value=1.0, or the PL value=0, and the PL value say be stored along with the paddle angles in the memory 142 to obtain depolarization information.

Acquisition of Information Indicating Depolarization

First, as in the first embodiment, the controller 140 performs normal OCT imaging on the eye E to be inspected (specifically, fundus Ef) with the paddle angles (θa1, θb1, and θc1) under the interference state to generate the tomographic image data (OCT image data). The OCT imaging here is imaging in the case of the first polarization state in which the controller 140 controls the polarization adjusting unit 170 so that the polarization state of the sample light and the polarization state of the reference light match with each other, and the OCT image data obtained through the imaging corresponds to the first image data (first OCT image data).

Next, the controller 140 drives the stepping motors 174, 175, and 176 with the values (Stmin1, Stmin2, and Stmin3) stored in the memory 142, and performs the OCT imaging with the paddle angles (θa2, θb2, and θc2) under the noninterference state to generate OCT image data. The OCT imaging here is imaging in the case of the second polarization state in which the controller 140 controls the polarization adjusting unit 170 so that the polarization state of the sample light and the polarization state of the reference light differ from each other, and the OCT image data obtained through the imaging corresponds to the second image data (second OCT image data).

In a case where a reflecting layer of the object maintains the polarization of the reflected and scattered light with respect to the incident light, when the imaging is performed with the paddle angles (θa1, θb1, and θc1) under the interference state, a strong interference signal is obtained, and an interference signal from a layer with a large difference in polarization of the reflected and scattered light with respect to the incident light is weak. In contrast, when the imaging is performed with the paddle angles (θa2, θb2, and θc2) under the noninterference state, interference between light from the site in which the polarization is maintained and the reference light is weak, while interference between the reflected and scattered light from the site with the large difference in polarization and the reference light is strong.

Therefore, with the first OCT image data expressed as I_max(x,z) and the second OCT image data expressed as I_min(x,z) as in the expression (2), the CPU 143 uses the above-mentioned two PL values PL1 and PL2 to acquire the image data I_np(x,z) indicating the depolarization by performing processing expressed by the following expression (3):

$$I\_np(x,z)=(I\_\max(x,z)-I\_\min(x,z))/(PL1-PL2) \quad (3).$$

In other words, in the expression (3), a first difference value (I_max(x,z)−I_min(x,z)) and a second difference value (PL1-PL2) are used to acquire the image data I_np(x, z) indicating the depolarization. The image data I_np(x,z) indicating the depolarization expresses the slope of the graph of FIG. 9 as described above. However, when a variation among models is not an issue of importance, the expression (2) described in the first embodiment may be used to acquire the image data I_np(x,z) indicating the depolarization.

Third Embodiment

Next, a third embodiment of the present invention is described.

In the first and second embodiments described above, the example in which the polarization adjusting unit 170 of the paddle type is used as the adjusting unit configured to adjust the polarization state of the interference light has been described, but the present invention is not limited thereto. For example, an in-line polarization adjusting unit or another adjusting unit may be used as the adjusting unit. In the third embodiment, there is described a case of using an adjusting unit that is different from the polarization adjusting unit 170 of the paddle type in the first and second embodiments.

Figure 10:
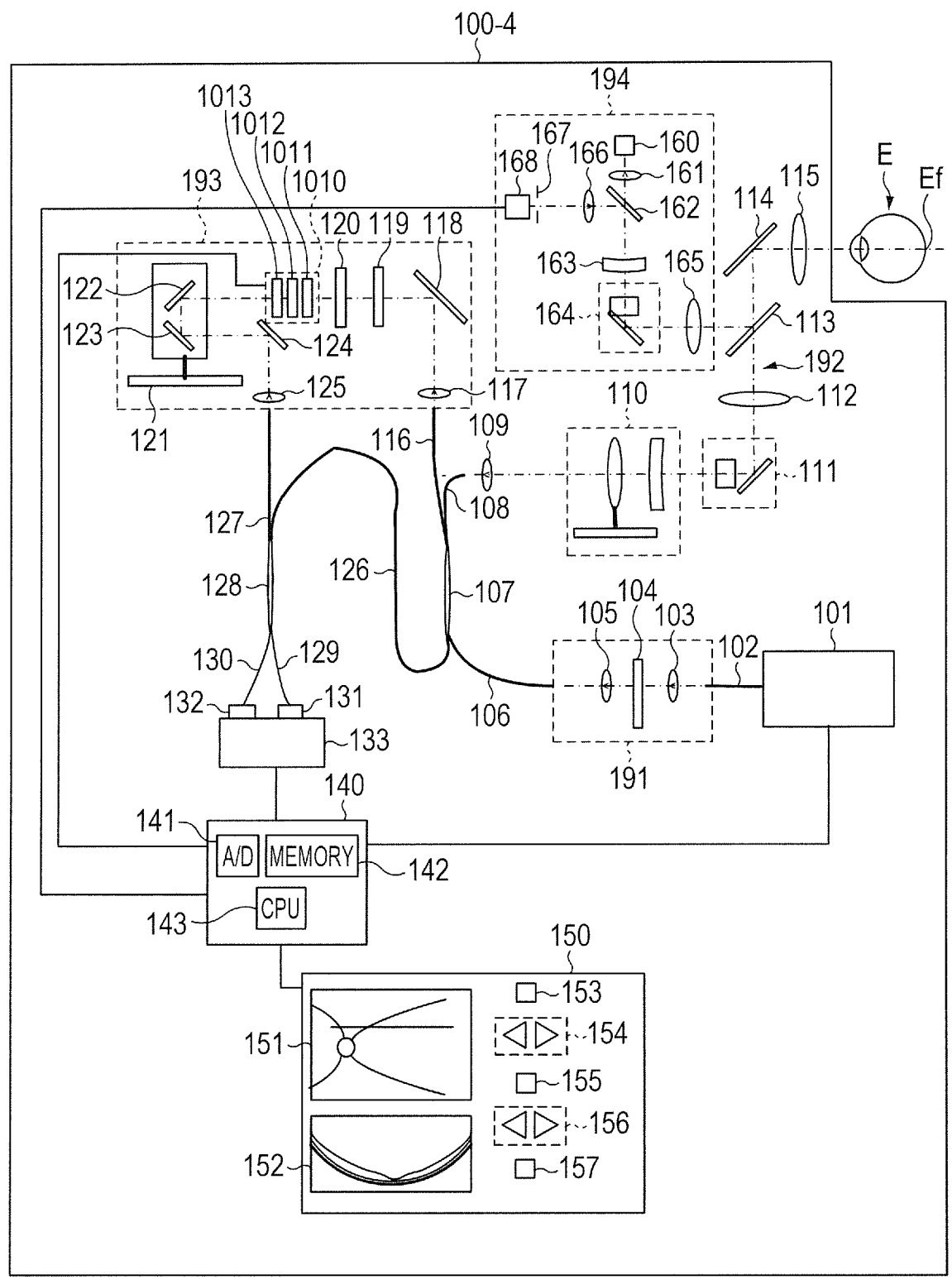
FIG. 10 is a diagram for illustrating an example of a schematic configuration of an ophthalmic imaging apparatus according to a third embodiment of the present invention.

FIG. 10 is a diagram for illustrating an example of a schematic configuration of an ophthalmic imaging apparatus 100 according to the third embodiment of the present invention. In FIG. 10, components similar to those of the ophthalmic imaging apparatus 100-1 according to the first embodiment illustrated in FIG. 1 are denoted by the same reference symbols, and the ophthalmic imaging apparatus 100 illustrated in FIG. 10 is referred to as "ophthalmic imaging apparatus 100-4".

In the ophthalmic imaging apparatus 100-4 illustrated in FIG. 10, instead of the polarization adjusting unit 170 illustrated in FIG. 1, the reference optical system 193 includes a polarization adjusting unit 1010 including a ¼λ wave plate 1011, a ½ wave plate 1012, and a ¼ wave plate 1013. The ¼λ wave plate 1011, the ½ wave plate 1012, and the ¼ wave plate 1013 are arranged in the reference optical system 193 to be adjustable to rotate with the optical axis being an axis of rotation, and an angle of the rotation may be adjusted by the controller 140 to perform polarization adjustment similar to that performed by the polarization adjusting unit 170 including the polarization adjusting paddles in the first and second embodiments described above.

Other Embodiments

In each of the embodiments of the present invention described above, there has been described a mode in which the polarization adjusting unit 170 (or polarization adjusting unit 1010) is arranged in the reference optical system 193 to adjust the polarization state of the reference light, but the present invention is not limited to the mode. For example, a mode in which the polarization adjusting unit 170 (or polarization adjusting unit 1010) is arranged in the sample optical system 192 to adjust the polarization state of the sample light is also encompassed by the present invention. Further, a mode in which the polarization adjusting unit 170 (or polarization adjusting unit 1010) is arranged in both of the reference optical system 193 and the sample optical system 192 to adjust the polarization state of the reference light and the polarization state of the sample light is also encompassed by the present invention.

Moreover, in each of the embodiments of the present invention described above, the imaging has been performed in two patterns of the interference state (first polarization state) and the noninterference state (second polarization state). However, a mode in which the paddle angles (angles of rotation of the wave plates) under the polarization adjusted state corresponding to the PL value, or values of actuators corresponding to the angles are stored so that a tomographic image under a state of a freely-selected PL value can be acquired, and so that a contrast between the polarization maintaining sites and the depolarization sites can be adjusted is also encompassed by the present invention. According to this mode, usability can be further increased.

Moreover, in each of the embodiments of the present invention described above, the example of acquiring the two-dimensional image data indicating the depolarization has been described, but the present invention is not limited thereto. For example, the fundus Ef may be two-dimensionally scanned through use of the optical scanning member 111 to acquire a first set of three-dimensional image data Int_max(x,y,z) and a second set of three-dimensional image data Int_min(x,y,z), and using those sets of three-dimensional image data, three-dimensional image data Int_np(x,y,z) indicating the depolarization may be acquired by the following expression (4):

$$Int\_np(x,y,z)=(Int\_max(x,y,z)-Int\_min(x,y,z))/(PL1-PL2) \qquad (4).$$

Through acquisition of three-dimensional image data indicating the depolarization, 3D volume data indicating the depolarization degree can be generated. As in the known methods, a front image can also be generated by adding data in a freely-selected range in a z direction.

Other Embodiments

Embodiment (s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment (s) and/or that includes one or more circuits (e.g., application specific integrated circuit (ASIC)) for performing the functions of one or more of the above-described embodiment (s), and by a method performed by the computer of the system or apparatus by, for example, reading out and executing the computer executable instructions from the storage medium to perform the functions of one or more of the above-described embodiment (s) and/or controlling the one or more circuits to perform the functions of one or more of the above-described embodiment (s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage median; may include, for example one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-075964, filed Apr. 6, 2017, which is hereby incorporated by reference herein in its entirety.

What is claimed is:

1. An ophthalmic imaging apparatus, comprising:
a combining unit, which is configured to combine, after light emitted from a light source is divided into measuring light and reference light, (a) sample light, which is returned from an eye to be inspected irradiated with the measuring light, and (b) the reference light to obtain interference light;
an adjusting unit, which is configured to adjust a polarization state of at least one of the sample light or the reference light; and
an acquiring unit, which is configured to acquire information on depolarization of the eye to be inspected through use of an intensity of first interference light, which is obtained when a polarization state of the sample light and a polarization state of the reference light are in a first relationship, and an intensity of second interference light, which is obtained when the polarization state of the sample light and the polarization state of the reference light are adjusted to establish a second relationship, which is different in matching degree from the first relationship.

2. An ophthalmic imaging apparatus according to claim 1, further comprising a generating unit, which is configured to generate first image data of the eye to be inspected using the information about the intensity of the first interference light, and to generate second image data of the eye to be inspected using the information about the intensity of the second interference light,
wherein the acquiring unit is configured to acquire third image data as information indicating the depolarization through use of the first image data and the second image data.

3. An ophthalmic imaging apparatus according to claim 2, wherein the acquiring unit is configured to perform subtraction on the first image data and the second image data to acquire the third image data.

4. An ophthalmic imaging apparatus according to claim 3, wherein the acquiring unit is configured to acquire the third image data through use of a first difference value which is obtained by performing subtraction on the first image data and the second image data, and a second difference value which is obtained by performing subtraction on the first matching degree value and the second matching degree value.

5. An ophthalmic imaging apparatus according to claim 1, further comprising a calculating unit, which is configured to calculate a matching degree value, which indicates a matching degree between the polarization state of the sample light and the polarization state of the reference light,
wherein the acquiring unit is configured to acquire the third image data through use of the first image data, the second image data, a first matching degree value which is the matching degree value at a time when the intensity of the first interference light is obtained, and a second matching degree value which is the matching degree value at a time when the intensity of the second interference light is obtained.

6. An ophthalmic imaging apparatus according to claim 1, wherein the first polarization state is a state in which the polarization state of the sample light and the polarization state of the reference light match with each other.

7. An ophthalmic imaging apparatus according to claim 6, wherein the second polarization state is a state in which the polarization state of the sample light and the polarization state of the reference light differ from each other.

8. A method of controlling an ophthalmic imaging apparatus, the ophthalmic imaging apparatus including a combining unit, which is configured to combine, after light emitted from a light source is divided into measuring light and reference light, (a) sample light, which is returned from an eye to be inspected irradiated with the measuring light, and (b) the reference light, to obtain interference light, the method comprising:

adjusting a polarization state of at least one of the sample light or the reference light; and acquiring information on depolarization of the eye to be inspected through use of an intensity of first interference light, which is obtained when a polarization state of the sample light and a polarization state of the reference light are in a first relationship, and an intensity of second interference light, which is obtained when the polarization state of the sample light and the polarization state of the reference light is are adjusted to establish a second relationship, which is different in matching degree from the first relationship.

9. A non-transitory computer-readable storage medium storing a program for causing a computer to execute the method according to claim 8.

* * * * *